United States Patent [19]

Eibofner et al.

[11] 4,175,323
[45] Nov. 27, 1979

[54] DENTAL HANDPIECE

[75] Inventors: Eugen Eibofner; Heinz Balsys, both of Biberach an der Riss, Fed. Rep. of Germany

[73] Assignee: Kaltenbach & Voigt GmbH & Co., Biberach an der Riss, Fed. Rep. of Germany

[21] Appl. No.: 852,601

[22] Filed: Nov. 15, 1977

[30] Foreign Application Priority Data

Aug. 11, 1977 [DE] Fed. Rep. of Germany ....... 2736285

[51] Int. Cl.$^2$ .............................................. A61C 1/12
[52] U.S. Cl. .................................................. 433/126
[58] Field of Search ...................... 32/27, 26, DIG. 1

[56] References Cited

U.S. PATENT DOCUMENTS

| 348,131 | 8/1886 | Lea ........................................ 32/27 |
| 756,336 | 4/1904 | Crawford ................................ 32/27 |
| 2,043,028 | 6/1936 | Blair ........................................ 32/27 |
| 2,319,328 | 5/1943 | Kaltenbach ............................. 32/27 |

FOREIGN PATENT DOCUMENTS

| 1077823 | 3/1960 | Fed. Rep. of Germany .............. 32/27 |
| 699351 | 12/1964 | Fed. Rep. of Germany ...... 32/DIG. 1 |
| 2359506 | 10/1975 | Fed. Rep. of Germany .............. 32/26 |
| 354893 | 7/1961 | Switzerland ....................... 32/DIG. 1 |

Primary Examiner—Louis G. Mancene
Assistant Examiner—John J. Wilson
Attorney, Agent, or Firm—Haseltine, Lake & Waters

[57] ABSTRACT

A dental handpiece in which supply lines run axially inside a longitudinal sleeve. This sleeve and the supply lines are divided transversely to form several handpiece sections. Each one of two facing ends of two adjacent handpiece sections have an axially projecting sleeve into which the end of the other handpiece section can be inserted. Two ends of the adjacent handpiece sections have a screw thread each. The thread may be an inside thread of the projecting sleeve forming a pipe-stub or nipple like threaded portion of the end inserted in the sleeve of the other handpiece section. One of the two pipe-stub like threaded portions has at least one cutout extending axially from its free end and is radially spring-like pretensioned in the unthreaded state of the two adjacent handpiece sections away from the other threaded portion with threads not engaged. This one of two pipe-stub like threaded portions, furthermore is rotatable relative to one engaging portion of the handpiece section which has a threaded portion with at least one cutout about an axis of the latter.

10 Claims, 8 Drawing Figures

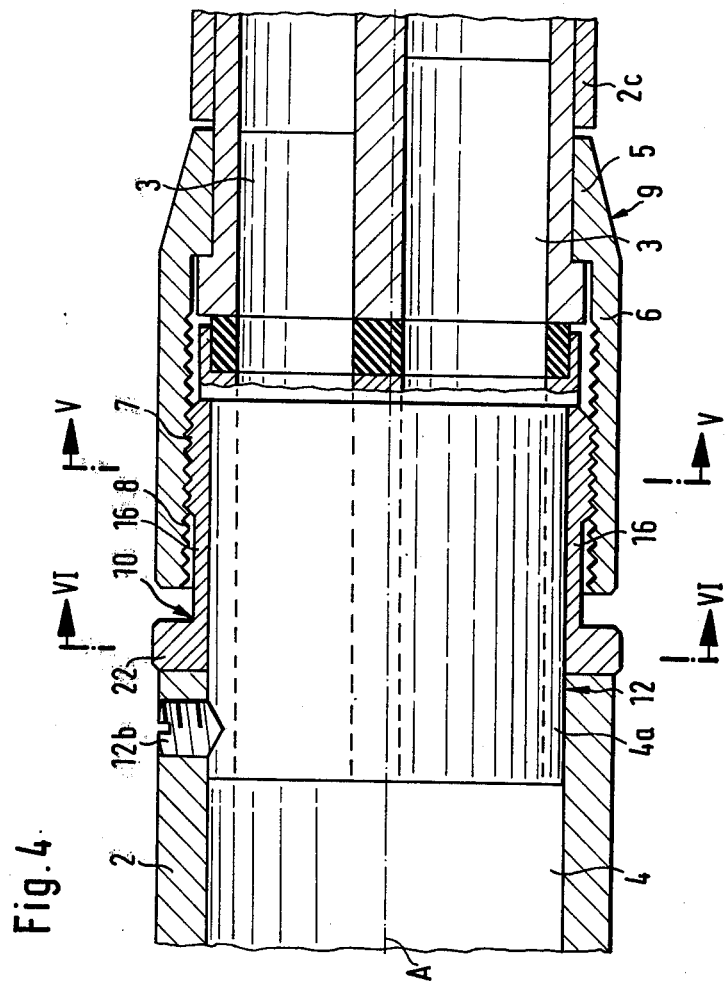

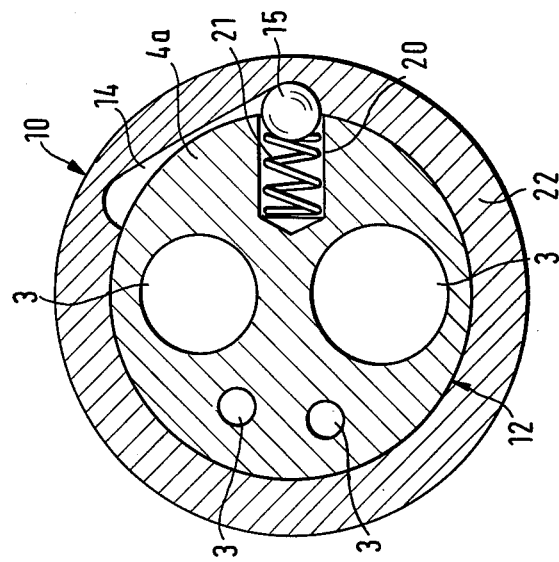
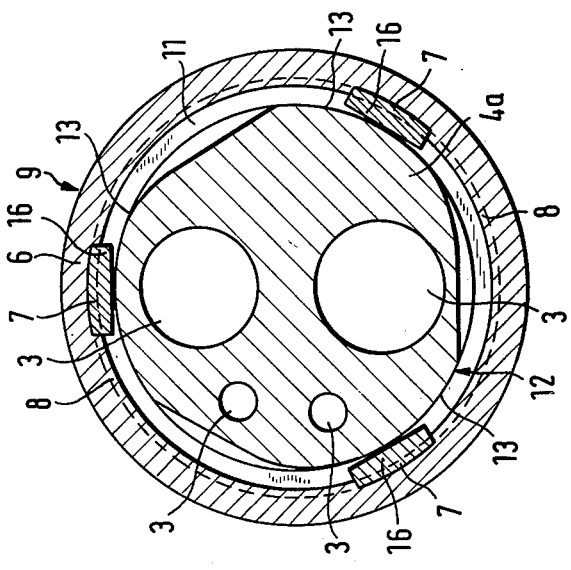

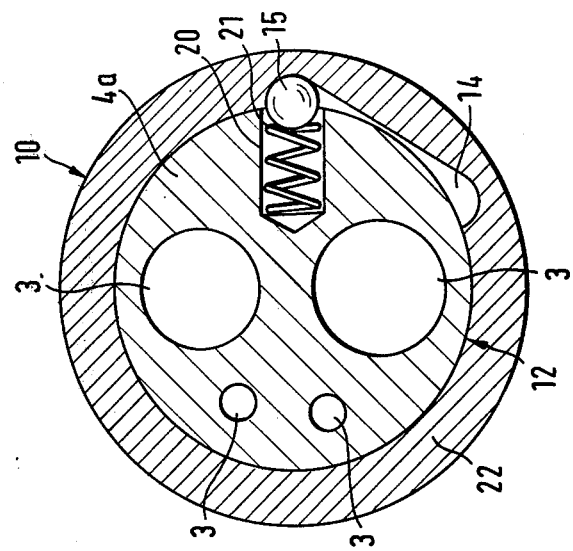
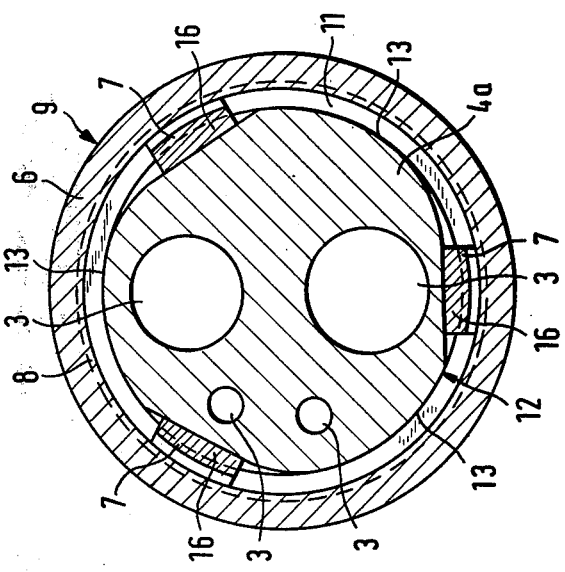

DENTAL HANDPIECE

BACKGROUND OF THE INVENTION

The present invention relates to a dental handpiece with supply lines running axially inside a longitudinal handpiece jacket. The handpiece jacket and the supply lines are divided transversely to form several handpiece sections and each of one of the two ends of two adjacent handpiece sections have an axially projecting sleeve in which the end of the other handpiece section can be inserted; the two ends for the detachable connection of the adjacent handpiece sections are provided with a screw thread each, either as inside thread of the projecting sleeve forming a pipe connection-like threaded portion of one handpiece section, or as outside thread of the handpiece sleeve also forming a pipe stub like threaded portion of the end inserted in the sleeve of the other handpiece section. In order to supply the inside of such a handpiece, e.g., bearing parts or rotating parts with oil or another lubricant, the above screw connection is disconnected so that the lubricant can be introduced from the partition portion into the corresponding handpiece section. Such lubrication is performed several times a day.

Such a dental handpiece is known from German Patent 11 16 860. With this known handpiece, the screwing and unscrewing of the adjacent handpiece sections, because of the many threads required by a sufficiently stable connection of the handpiece sections, requires much time. It has been found that because of the great time consumption, lubrication of the handpieces is frequently neglected so that they are damaged.

From the German Laid Open Document 23 59 506 it is known how to connect a quick-connection unit fixedly to the screw threads at the end of the two adjacent handpiece sections. The quick-connection comprises a bayonet catch and involves relatively high cost. The advantage of quick actuation is negated by the high cost.

Finally, the Swiss Patent No. 354,893 shows a similar dental handpiece, where the ends of the adjacent handpiece sections have no threads. The end, to be inserted in the sleeve of one handpiece section, and of the other handpiece section, has an external torus which during the connection of adjacent handpiece sections engages an internal annular groove of the elastic sleeve. After effecting this engagement, a locking sleeve must be slid from the handpiece section having the sleeve in the axial direction over the elastic sleeve. Aside from the fact that the insertion of the handpiece section with the torus into the elastic sleeve and the sliding over of the locking sleeve is difficult and time consuming, a tight connection of the supply lines of the two adjacent handpiece sections cannot be achieved.

Accordingly, it is an object of the present invention to provide a dental handpiece of the type described initially, where the screw threads of two adjacent handpiece sections can be connected and disconnected quickly and safely, avoiding much cost, while simultaneously ensuring tight connection of the supply lines of the two adjacent handpiece sections.

Another object of the present invention is to provide a dental handpiece of the foregoing character which may be economically fabricated and easily maintained in service.

A further object of the present invention is to provide a dental handpiece, as described, which has a substantially long operating life.

SUMMARY OF THE INVENTION

The objects of the present invention are achieved by providing that one of the two pipe-stub like threaded portions has at least one perforation extending axially from its free end and is radially springlike pretensioned in the unthreaded state of the two adjacent handpiece sections away from the other threaded portion, with the threads not engaged, and is rotatable relative to one engaging portion of the handpiece section provided with the threaded portion having at least one perforation about the axis of this handpiece section; the engaging portion is provided with startup areas or cams which can be placed on the afore-mentioned threaded portion and radially moving the latter during the relative rotation of threaded portion and engaging portion against the spring-like pretension towards the thread of the other threaded portion till the two threaded portions are engaged; the threaded portion having at least one perforation is rotatable relative to its handpiece section about the axis of the latter, and is provided with counter engagement means provided at this handpiece section for pushing together the ends of the two adjacent handpiece sections during the relative rotation of threaded portion and handpiece section.

To connect two separate adjacent handpiece sections, one handpiece section need merely be inserted by the pipe-stub like threaded portion carrying the outside thread into the pipe-stub like threaded portion having the inside thread; then the threaded portion having at least one perforation and the associate engaging section need only be twisted briefly relative to each other; because of the contact of start-up surfaces and cams of the engaging section, beginning immediately after starting the twisting and acting in the radial direction, with the spring-like pretensioned threaded portion, the thread of the latter very quickly engages the thread of the other threaded portion; immediately after this engagement, by relative twisting of the threaded portion having at least one perforation, and the handpiece section on which this threaded portion is located, the engaging means engaging the counter engaging means of the mentioned handpiece section bring about a pressing together of the ends of the two adjacent handpiece sections, with mutual sealing of the ends of the supply lines of the two handpiece sections. Because the handpiece in accordance with the present invention, in comparison with the handpiece known from German Patent No. 11 16 860 remains unchanged on the end of one handpiece, the advantage of quick actuation with mutual sealing of the aforementioned supply lines is combined with the advantage of relatively small effort.

Expediently, the engaging means and the counter engaging means for pressing together the ends of the two adjacent handpiece sections, comprises a helical guide slot provided in the threaded portion having at least one perforation and a radial cam projecting into the guide slot and located on the handpiece section.

The relative twisting between the threaded portion having at least one perforation and the engaging section may be restricted, e.g., by the ends of the guide slot. In a similar manner, the relative twist between the mentioned threaded portion and the handpiece section on which the threaded portion is located may be restricted. It is expedient to provide resilient detents at the restrictions of the aforementioned relative twists, e.g., in the form of a recess located on the one rotary portion and a detent body detenting on the other rotary section under the action of a spring, e.g., a detent ball.

The afore-mentioned threaded portion may have three perforations. If the threaded portion has two or more perforations, the threaded portion parts remaining between the perforations are in the form of spring-like tongues.

A convenient embodiment has the following improvement: The engaging portion is formed by a cap sleeve rotary at the end of the one handpiece section about the axis of the latter; its inside wall has the start-up surfaces or cams which, acting radially from the outside to the inside can be placed against the threaded portions or the spring-like tongues of the threaded portion located inside the cap sleeve and forms the sleeve into which the end of the other handpiece section is inserted, with three start-up surfaces or cams distributed over the periphery.

In this embodiment, a twisting of the cap sleeve results in a twisting of the cap sleeve itself relative to the threaded portion having at least one perforation, and a common twisting of the cap sleeve with the afore-mentioned threaded portion relative to the handpiece section carrying the mentioned threaded portion. After the initial twist of the cap sleeve has resulted in the engagement of the threads of the two threaded portions, the relative twisting of the threaded portion and the handpiece sections starts, resulting in the above-mentioned pressing together of the ends of the two handpiece sections to be connected.

With this embodiment it is expedient if, to restrict the relative twist between threaded portion and cap sleeve, the latter at its inside has a cam which engages a slot extending over a part of the periphery of the threaded portion.

A second expedient embodiment has the following improvement: the engaging part is formed by the end of the handpiece section; at the outside of this handpiece section, there are start-up surfaces or cams which can be placed against the threaded portion acting from the inside to the outside, or against the spring-like tongues of the threaded portion which is rotary on the handpiece section end forming the engaging part and is inserted in the sleeve located on the end of the other handpiece section. The sleeve constitutes the other threaded portion and may be rotary or stationary on the afore-mentioned other handpiece section.

With this embodiment, while twisting the threaded portion which is accessible from the outside, is provided with a grip ring and has at least one perforation, relative to the handpiece section on which the afore-mentioned threaded portion is located, first the thread of this threaded portion is made to engage the thread of the sleeve constituting the other threaded portion; then, when continuing to twist the first threaded portion, its engaging means and the counter engaging means of the afore-mentioned handpiece section in the sense of pressing together the ends of the two handpiece sections enter into action.

With this embodiment it is expedient if the guide slot is a groove located on the inside wall of the pipe-stub like threaded portion and the radial cam is an engaging body located in a radial recess of the handpiece section and projecting under the action of a spring into the groove, e.g., a ball.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 4 shows a lengthwise section of the zone of transverse division of a dental handpiece in a second embodiment corresponding to FIG. 1, with the two threaded portions engaged;

FIG. 5 shows a section taken along line V—V in FIG. 4;

FIG. 6 shows a section taken along line VI—VI in FIG. 4;

FIG. 7 shows the view of FIG. 5 with the two threaded portions not engaged; and

FIG. 8 shows the view of FIG. 6 with the two threaded portions not engaged.

DESCRIPTION OF THE PREFERRED EMBODIMENTS

Figure 1:
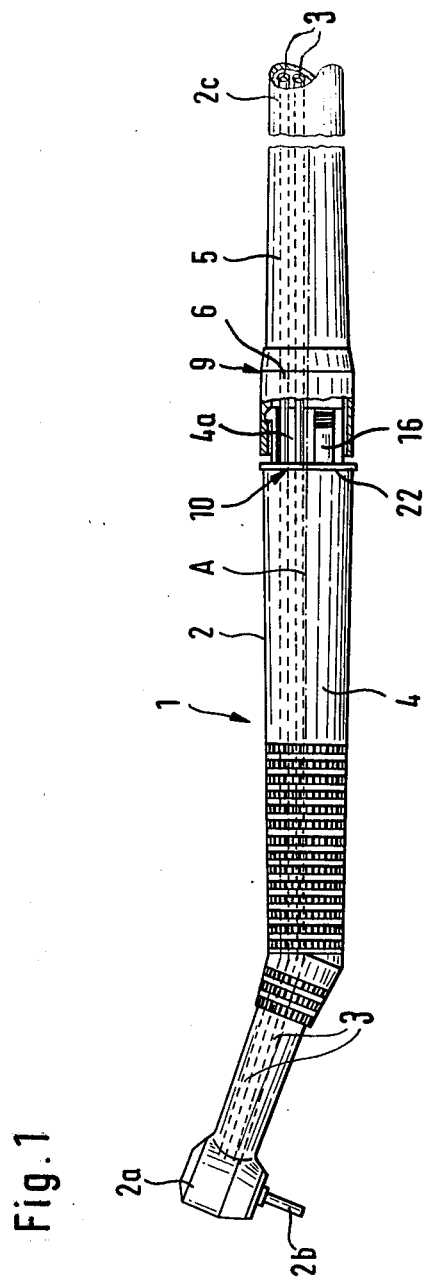
FIG. 1 shows a dental handpiece in a side sectional view in the zone of transverse division.

Referring to FIG. 1, the dental handpiece 1 has a longitudinal handpiece sleeve 2 with supplying lines 3 running on the inside parallel to the handpiece axis A. Through the supply lines 3, are applied energy (power) or a medium, e.g., an electric current for an electric drive motor (not shown) in handpiece 1, compressed air for a turbine (not shown) located in the head 2a, cooling air and/or cooling water for the tool 2b mounted in head 2a. The supply lines 3 are connected via connecting lines (not shown) located in a flexible supply hose 2c with energy or medium sources (also not shown).

Figure 2:
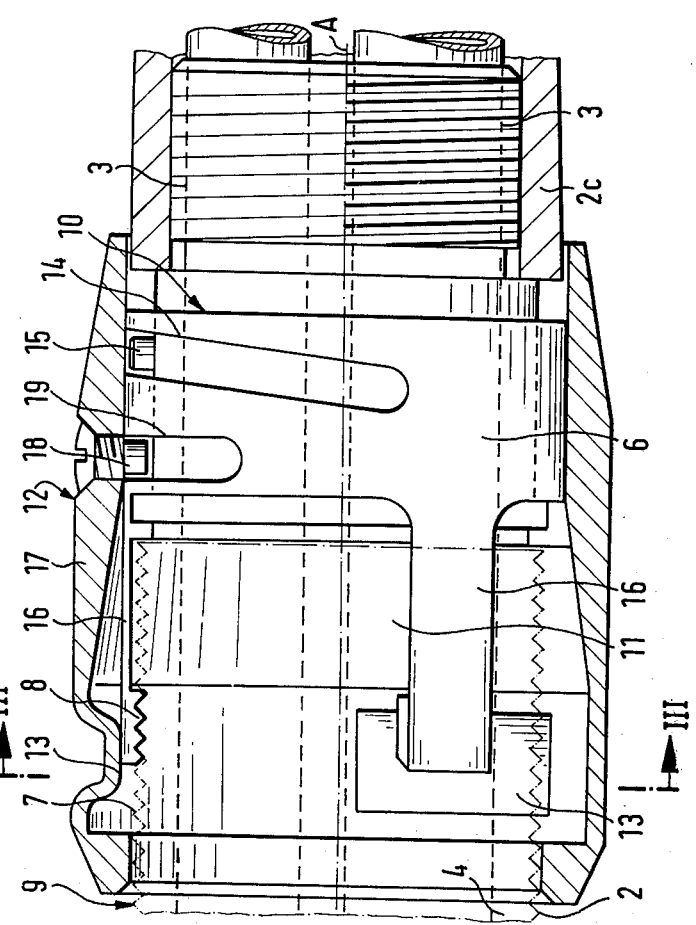
FIG. 2 shows a lengthwise section of the zone of transverse division of a dental handpiece in a first embodiment, with the two threaded portions engaged.

The handpiece sleeve 2 and the supply lines 3 are divided transversely forming several, in this case two handpiece sections 4, 5 according to FIGS. 1, 2 and 4. One of the two handpiece sections 4, 5 adjacent to the two ends has an axially projecting sleeve 6 in which the end of the other handpiece section can be inserted. The facing ends of the two handpiece sections 4, 5 form a detachable connection and are provided with a screw thread 7, 8 which is the inside thread 8 of sleeve forming a pipe-stub like threaded portion 9 of the end of the handpiece section 5, and as outside thread 7 of the handpiece sleeve 2 it also forms a pipe-stub forming threaded portion 10 of handpiece section 4.

One of the two pipe-stub like threaded portions, the threaded portion 10 on the left in FIGS. 1 and 4 and on the right in FIG. 2 is provided with three cutouts 11, starting from its free end and extending axially, with the parts of threaded portion 10 remaining between the cutouts 11 having the form of spring-like tongues. The spring-like tongues 16 are radially pretensioned in the disconnected state of the adjacent handpiece sections 4, 5 in the direction away from the other threaded portion 9 with the threads 7, 8 disengaged.

The threaded portion 10, provided with the cutouts 11 and the spring-like tongues 16, can be rotated about axis A relative to that handpiece section 4 or 5 on which it is located. The engaging part 12 is provided with start-up surfaces or cams 13 which can be placed against the spring-like tongues 16 of the threaded portion 10 and move the spring-like tongues 16 in radial direction during the relative rotation of threaded portion 10 and engage part 12 against the spring-like pretension toward the thread of the other threaded portion 9 till threads 7, 8 of both threaded portions 9, 10 are engaged. With the embodiment of FIGS. 1 and 4 to 8, this movement is radially outward and with the embodiment of FIGS. 2 and 3 radially inward, as indicated by the different design of engaging portion 12, to be discussed later.

The threaded portion 10 provided with the cutouts 11 and the spring-like tongues 16 can be rotated about axis A relative to the handpiece section 4 or 5 on which it is located. Also, the threaded portion 10 has engaging means 14 engaging the counter engaging means provided on the mentioned handpiece section. The engaging means 14 and the counter engaging means 15, during relative rotation of threaded portion 10 and handpiece section 4 or 5 pull together the ends of the two adjacent handpiece sections 4, 5 so that a tight connection of the supply lines 3 from one handpiece section to those of the other handpiece section is ensured.

As shown in FIGS. 2, 6 and 8, the engaging means 14 comprise a helical guide slot 14 in the threaded portion, while the counter engaging means 15 are formed by a radial cam 15, provided at the handpiece section belonging to threaded portion 10 and projecting into the guide slot. With proper rotation of the threaded portion 10, it moves along axis A towards the right in FIG. 2 and along axis A towards the left in FIGS. 1 and 4. In any case, the other handpiece section 4 in FIG. 2 and the other handpiece section 5 in FIGS. 1 and 4 is pulled towards the handpiece section carrying threaded portion 10, so that the above-mentioned connection of the supply lines 3 is ensured.

Figure 3:
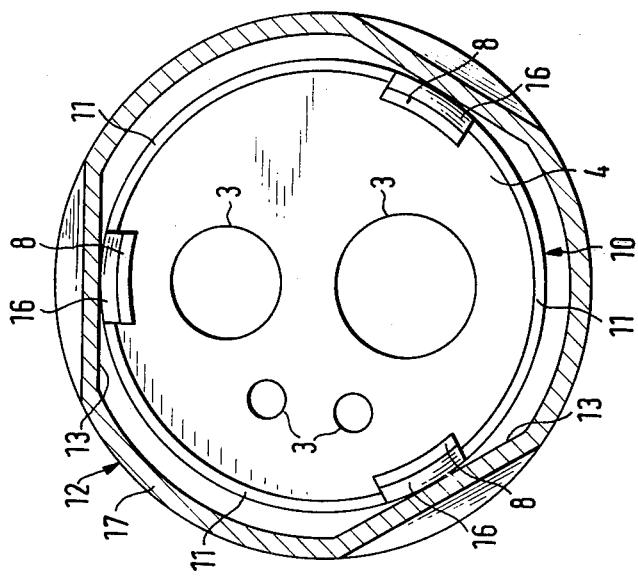
FIG. 3 shows a section taken along line III—III in FIG. 2.

This pulling together of handpiece sections 4 and 5 is possible because before during the twisting (rotation) of the threaded portion 10, the start-up surfaces or cams 13 have pressed the spring-like tongues 16 in the radial direction till threads 7, 8 were engaged so that the two handpiece sections 4, 5 are pulled together during twisting of threaded portion 10 via the engaged threads 7, 8. In the embodiment of FIGS. 2 and 3, the engaging portion 12 comprises a cap sleeve 17 rotatable about axis A at the end of the one handpiece section 5. On the inside wall of cap sleeve 17 are the start-up surfaces or cams 13 which rest against the spring-like tongues 16 of the threaded portion radially from the outside to the inside. The threaded portion 10 is located within the cap sleeve 17 and simultaneously constitutes sleeve 6 in which the end of the other handpiece section 4 is inserted.

To limit the relative rotation between threaded portion 10 and cap sleeve 17, the latter has at its inside wall a cam 18 which engages a slot extending over part of the periphery of the threaded portion with the ends of slot 19 forming the limits of relative rotation. According to FIG. 2, the cam 18 is formed by the shank of a screw passing through the wall of the cap sleeve 17. The relative rotation between threaded portion 10 and engaging portion 12 is formed by the ends of the guide slot 14.

With the other embodiment according to FIGS. 1 and 4 to 8, the engaging portion 12 comprises the left-hand handpiece section 4 in FIG. 4, where there is a special end section 4a which projects from the handpiece sleeve 2 and is secured by a setscrew 12b. On the outside of end section 4a are the start-up surfaces or cams 13 which, acting radially from the inside to the outside, move the spring-like tongues 16 of threaded portion 10 against the spring pretension till threads 7, 8 are engaged. With this embodiment, the threaded portion 10 rotates on the end section 4a and inserted in the sleeve 6 located at the end of the other handpiece section 5.

Also, in the embodiment of FIGS. 1 and 4 to 8, the guide slot 14 is a groove located on the inside wall of the pipe-stub like threaded portion 10 and the radial cam 15 is a ball projecting into the groove under the pressure of a helical spring, located in a radial hole 20 of the handpiece section 4.

For easier actuation, the threaded portion 10 according to FIGS. 1 and 4 has a radially outward projecting grip ring 22.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalents of the following claims.

We claim:

1. A dental handpiece comprising: supply lines running axially inside a longitudinal handpiece sleeve, with said handpiece sleeve and supply lines being divided transversely to form several handpiece sections, said handpiece sections having ends, one of two facing ends of two adjacent handpiece sections having an axially projecting sleeve into which the end of the other handpiece section can be inserted; two facing ends of adjacent handpiece sections having a screw thread each to form a detachable connection; said screw thread being an inside thread of the projecting sleeve forming a pipe-stub like threaded portion of the end inserted in the sleeve of the other handpiece section; an engaging portion; one of two pipe-stub like threaded portions having at least one cutout extending axially from the free end of said handpiece section and forming threaded spring-like tongues; said one of two threaded portions being radially spring-like pretensioned in the unthreaded state of the two adjacent handpiece sections away from the other threaded portion with threads not engaged, said one of two pipe-stub like threaded portions being rotatable relative to said engaging portion of the handpiece section having a threaded portion with at least one cutout about an axis of said handpiece section; said engaging portion having startup surfaces placeable on said threaded portion and radially moving said threaded portion during relative rotation of said threaded portion and said engaging portion against a spring-like pretension towards the thread of the other threaded portion till the threads of the two threaded portions are engaged; said threaded portion having at least one cutout being rotatable relative to its handpiece section about an axis thereof and having engagement means engaging counter engagement means on the last-mentioned handpiece section for pushing together the ends of said two adjacent handpiece sections during the relative rotation of said threaded portion and handpiece section; said engaging means and counter engaging means for pressing together the ends of the two adjacent handpiece sections comprising helical guide slot means in said threaded portion having at least one cutout; and a radial cam located on the handpiece section and projecting into said guide slot means.

2. A dental handpiece as defined in claim 1 wherein relative motion between said threaded portion having at least one cutout and said engaging portion is restricted.

3. A dental handpiece as defined in claim 1 wherein relative rotation between said threaded portion having at least one cutout and the associated handpiece section is restricted.

4. A dental handpiece as defined in claim 1 wherein one threaded portion has three cutouts.

5. A dental handpiece as defined in claim 1 wherein one threaded portion has at least two cutouts, parts of said threaded portion remaining between said cutouts having spring-like tongues.

6. A dental handpiece as defined in claim 1 wherein said engaging portion is formed by a cap sleeve rotatable on the end of one handpiece section about said axis thereof, said cap sleeve having an inside wall with said startup surfaces acting radially from the outside to the inside and placeable against the threaded portion simultaneously forming the sleeve into which the end of the other handpiece section is insertable.

7. A dental handpiece as defined in claim 6 wherein said cap sleeve has on its inside wall a cam engaging a slot extending over part of the periphery of said threaded portion for limiting relative rotation between said threaded portion and said cap sleeve.

8. A dental handpiece as defined in claim 1 wherein said engaging portion is formed by the end of a handpiece section, said handpiece section having an outside wall with start-up surfaces acting radially from the inside to the outside and placeable against the threaded portion and forming said engaging portion of the handpiece section and being insertable into the sleeve located at the end of the other handpiece section.

9. A dental handpiece as defined in claim 1 wherein said guide slot means comprises a groove located in the inside wall of said pipe-stub like threaded portion, and spring means, said radial cam comprising an engaging member located in a radial hole of the handpiece section and projecting into said groove under the influence of said spring means.

10. A dental handpiece as defined in claim 1 wherein relative motion between said threaded portion having at least one cutout and said engaging portion is restricted, one threaded portion having at least two cutouts, parts of said threaded portion remaining between said cutouts having spring-like tongues, said guide slot means comprising a groove located in the inside wall of said pipe-stub like threaded portion, and spring means, said radial cam comprising an engaging member located in a radial hole of the handpiece section and projecting into said groove under the influence of said spring means.

* * * * *